United States Patent [19]

Kaoru et al.

[11] Patent Number: 4,715,814
[45] Date of Patent: Dec. 29, 1987

[54] ARTICULATOR

[75] Inventors: Koide Kaoru, Niigata; Nagai Sadao, Urawa, both of Japan

[73] Assignee: Takamiya Dental Manufacturing Company Limited, Tokyo, Japan

[21] Appl. No.: 835,262

[22] Filed: Mar. 3, 1986

[30] Foreign Application Priority Data

Jun. 12, 1985 [JP] Japan .................. 60-127709

[51] Int. Cl.⁴ .......................................... A01C 11/00
[52] U.S. Cl. ........................................................ 433/59
[58] Field of Search .................... 433/59, 60, 61, 62

[56] References Cited

U.S. PATENT DOCUMENTS 3,159,915 12/1964 Bev et al. .................. 433/59

FOREIGN PATENT DOCUMENTS

48-10870 4/1973 Japan .

Primary Examiner—Robert Peshock
Attorney, Agent, or Firm—Holman & Stern

[57] ABSTRACT

This invention relates to an articulator for checking or deciding the biting state of dentures in the mouth by associating upper and lower jaw arciforms for mounting a gypsum model to fabricate the dentures and arbitrarily producing a relative positional relationship between the upper and the lower jaw arciforms. A condyle sphere formed on the lower jaw arciform is supported by a condyle path plate formed at the upper jaw arciform. The condyle path plate is composed of side, upper and lower walls, and can be used as an archon box type or an archon slot type by the operation of the condyle path plate.

4 Claims, 17 Drawing Figures

ARTICULATOR

BACKGROUND OF THE INVENTION

This invention relates to an articulator for deciding the biting state of dentures.

DESCRIPTION OF THE PRIOR ART

Articulators are sorted into archon type and condyle type. The archon type has in general excellent reproducibility of the motion in jaws. The archon type is further sorted into archon box type and archon slot type. Since the box type can readily separate between the upper and the lower jaw arciforms, the box type is adapted for manufacturing a crown bridge. The box type further has an advantage that a split cast is not necessarily produced in case of regulating the condyle path by a check biting method. However, since a condylar sphere is floated from the condyle path plate, this box type is not appropriate for fabricating a dental prosthesis.

The slot type does not float has, on the other hand, strong coupling between the upper and the lower jaw arciforms, and the condylar sphere is not floated even in operation, and an arrangement and a grinding operation of dentures can be effectively and readily carried out. Thus, the slot type is adapted for the dental prosthesis. Since the upper and the lower jaw arciforms cannot be generally readily separated, the slot type is not adequate for manufacturing a crown bridge. Further, when a condyle path is adjusted by a check biting method, a split cast must be produced at every time. In other words, both types have both advantages and disadvantages. Therefore, the type adapted for both types is sold in the market, but this type is of exchange type for exchanging components necessary to be used as an archon box type or archon slot type, in which complicated operations and adjustments of attaching and detaching the type are required, and important components are expensively required for two articulators.

SUMMARY OF THE INVENTION

An object of this invention is to provide an articulator which can all eliminate the drawbacks and disadvantages of the conventional archon box and slot types by employing the entire advantages of the both archon type and the condyle type to use a side method by the operation of one component.

In order to achieve the above object, the articulator 3 of this invention having an upper jaw arciform 1 and a lower jaw arciform 2 for mounting a gypsum model comprises a pair of right and left condylar spheres 4 and 4 provided at the rear of the lower jaw arciform, condyle path plates 5 provided at the rear of the upper jaw arciform for supporting the condylar spheres, the condyle path plates composed of a rear wall 6 contacted with the rears of the condyle spheres, side walls 7 contacted with the sides, and a lower wall 9 contacted with the lower portion for preventing the condyle path plate from floating.

Another object of this invention is to provide an articulator which comprises a lower wall at the condyle thereof for preventing the upper jaw from floating to eliminate the problem observed in the conventional archon type articulator, and maintains the longitudinal positional relationship between the upper jaw and the lower jaw irrespective of the variation in the length of the side condyle path angle or the length between the condyles, thereby rapidly and reliably handling the articulator.

DESCRIPTION OF THE PREFERRED EMBODIMENTS

An embodiment of this invention will now be described in detail with reference to the accompanying drawings.

A lower jaw arciform 2 has a pair of posts 17 and 18 stood at both sides of the rear, condyle shafts 19 are respectively projected oppositely from the upper inner ends of the posts, and condylar spheres 4 are respectively mounted at the inner ends of the shafts. The upper jaw arciform 1 is held to rise on the sphere 4 through a condyle path plate 5 pivotally secured to both rear sides via a shaft 10. The condyle path plates 5 are rotated around a rotational shaft 10 to alter the inclining angle of the condyle path. Reference numeral 20 designates a scale for indicating the condyle path of an arrow provided at a rotary member 15 integral with the condyle path plate 5, and numeral 21 depicts a clamping screw of the plate 5.

Figure 8:
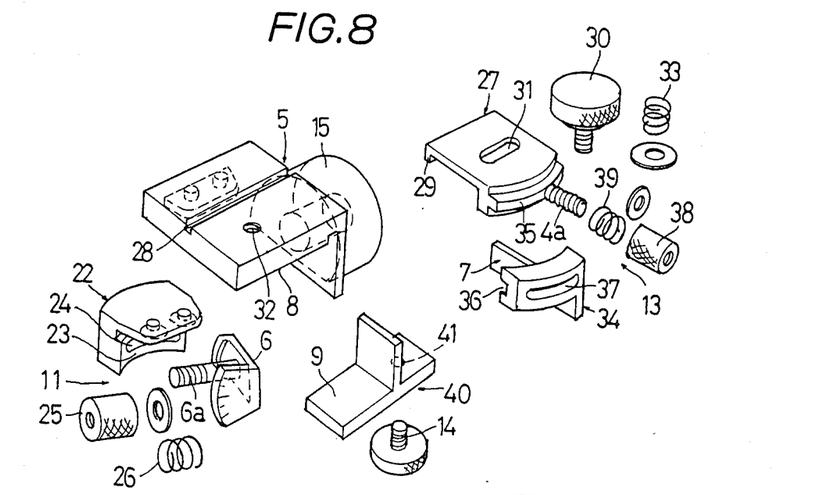
FIG. 8 is an exploded perspective view of the articulator.
Figures 9, 10:
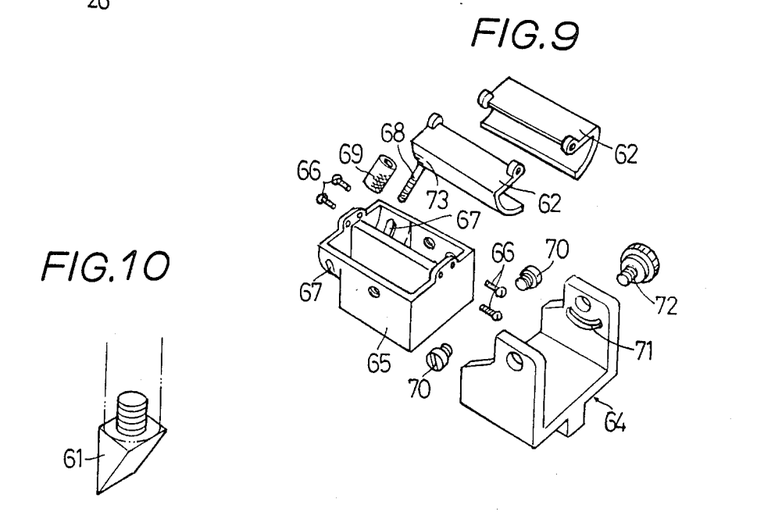
FIG. 9 is an exploded perspective view of a table on which an incisal pin chip is disposed.
FIG. 10 is a perspective view of a pin chip.
Figure 11:
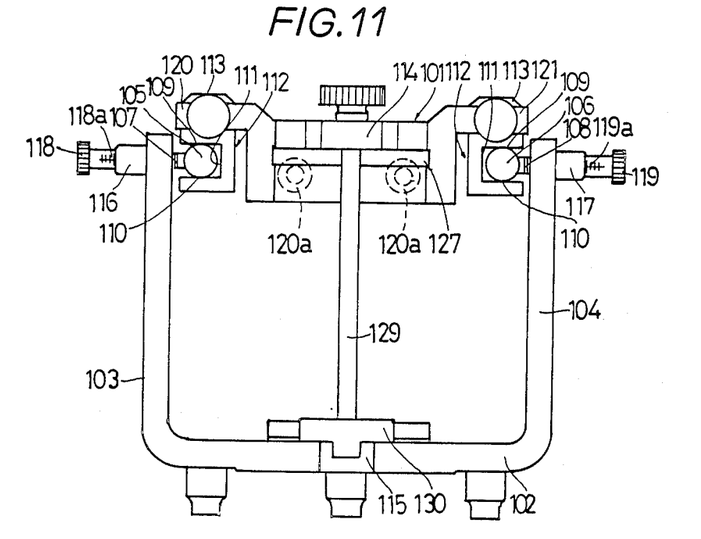
FIG. 11 is a front view.
Figure 12:
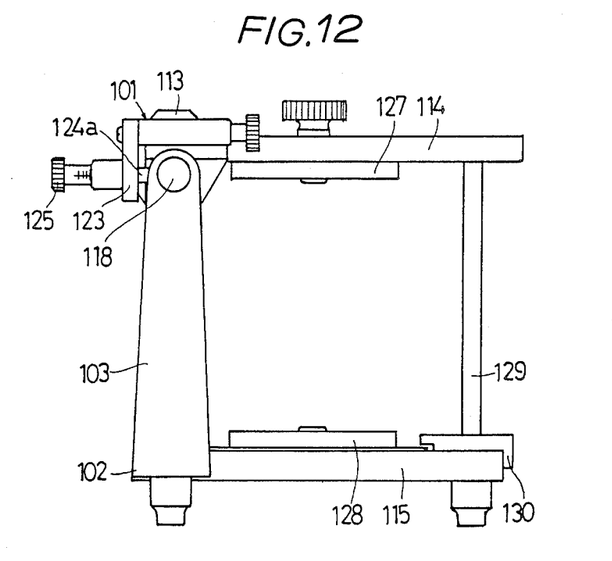
FIG. 12 is a left side view.
Figure 13:
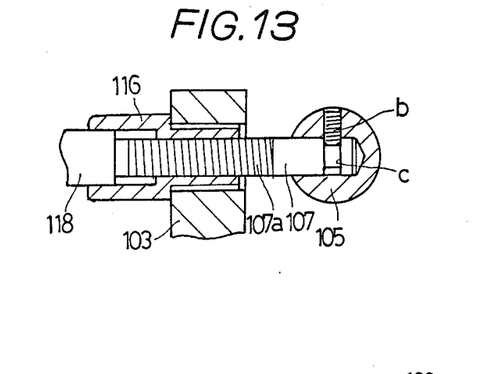
FIG. 13 is a sectional view of a condylar sphere mounting portion.
Figure 14:
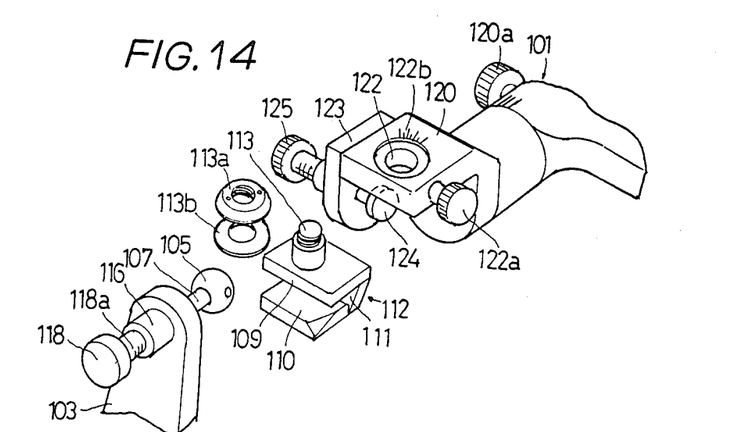
FIG. 14 is an exploded perspective view of the essential portion of this invention.
Figure 15:
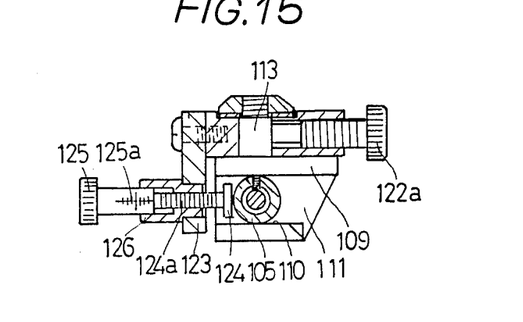
FIG. 15 is a sectional view of the condyle path.

The condyle path plate 5 is formed in an inverted L shape, has a horizontal portion, as exemplified in FIG. 8, which is an upper wall 8 contacted with the condylar sphere 4 on the lower surface, and is movably formed with a rear wall 6 at the rear, with side walls 7 at the inside, and with a lower wall 9 at the lower side. Reference numeral 22 indicates a rear wall support having an arcuate surface 23 with the sphere 4 as a center, numeral 24 illustrates a rear wall guide hole, through which a shaft 6a projected backward of the rear wall 6 is penetrated, numeral 25 designates a knob engaged with the shaft 6a, and numeral a tension spring for pulling backward the rear wall 6, which construct a slide mechanism 11 for altering the angle of the rear wall. Reference numeral 27 depicts a side plate mounting member having an engaging portion 29 to be engaged with a lateral groove 28 formed on the upper wall, numeral 30 indicates a spring for restricting the movement of the member 27 and the spring 30 is engaged with the hole 32 of the upper wall from the long hole 31 on the upper surface of the member. Numeral 33 illustrates a spring. Numeral 34 illustrates a side condyle path inclining angle restricting plate having a groove 36 to be engaged with an arcuate projection 35 at the front edge of the side plate mounting member 27, and the the restricting plate 34 has an inclining angle restricting hole 37, through which an inclining angle stationary shaft 4a is penetrated, is secured fixedly by a clamping screw 38, which construct a side wall moving mechanism 13. Numeral 39 designates a spring. Numeral 40 illustrates a lower wall contacting plate, and numeral 41 shows a hole for passing a mounting screw 14, and the lower wall 9 is detachably mounted on the lower surface of the rotary member 15. The inner end of the rotational shaft 10 of the condyle path plate 5 is projected into the central space 42 of the upper jaw arciform 1, arranged so as not to cause a fluctuation by a detent member 16. Thus, the accurate side shifting is proved to eliminate no distinction from the mechanical error.

Figure 1:
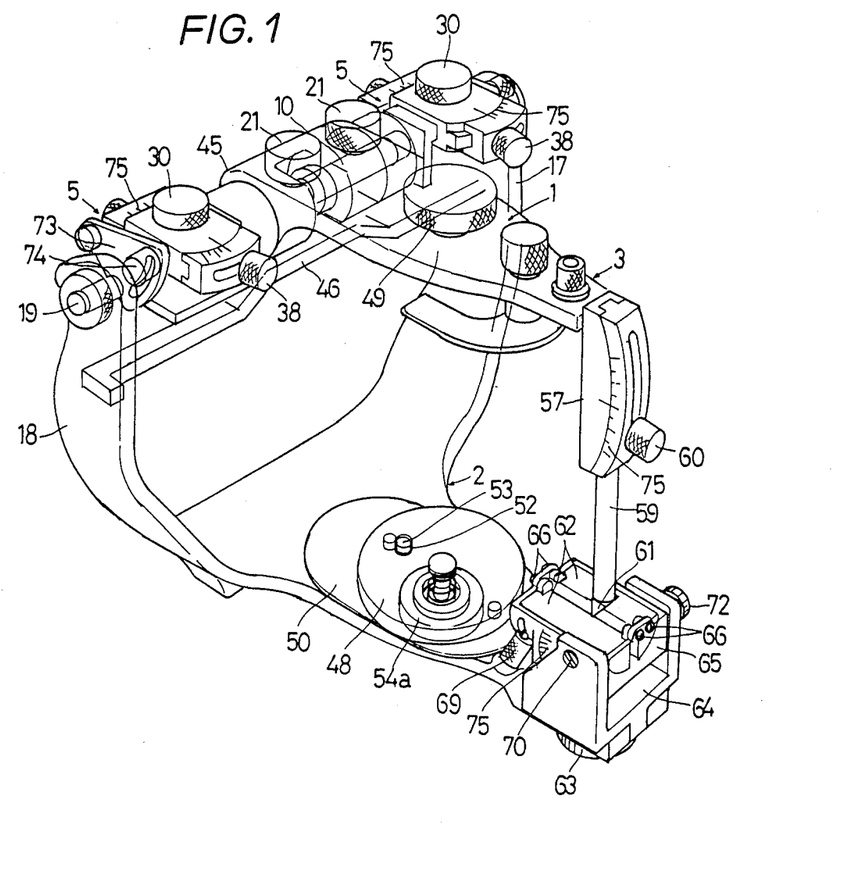
FIG. 1 is a perspective view of an embodiment of an articulator constructed according to this invention.
Figure 2:
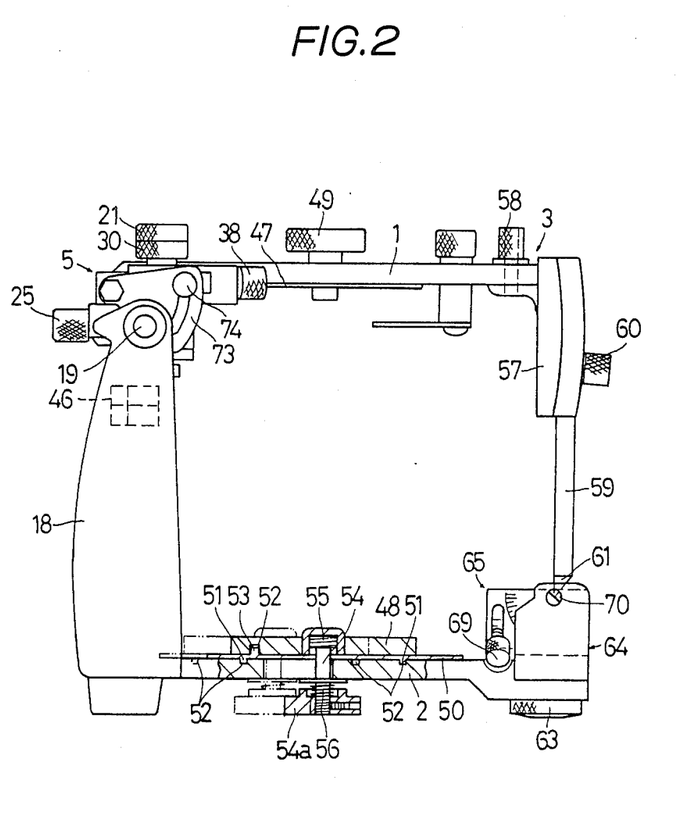
FIG. 2 is a side view of the articulator in FIG. 1.
Figure 3:
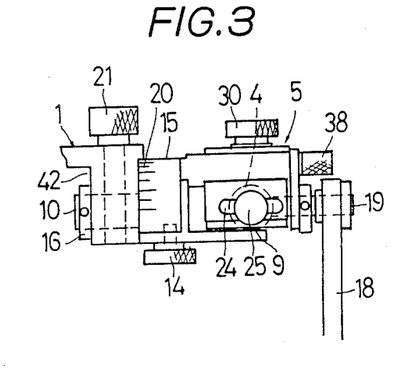
FIG. 3 is a front view of the condyle path plate.
Figure 4:
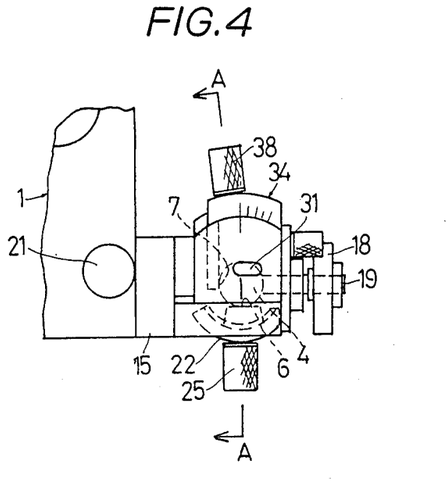
FIG. 4 is a top view of the condyle path plate.
Figure 5:
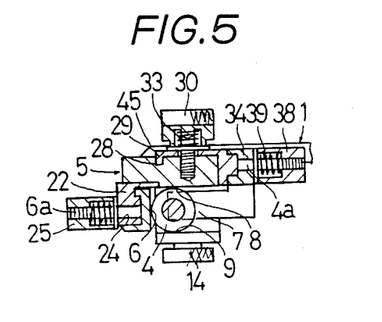
FIG. 5 is a sectional view, taken along the line A—A of FIG. 4.
Figure 6:
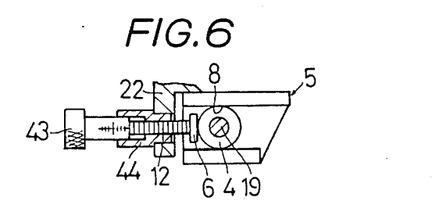
FIG. 6 is a sectional view showing a partly modified embodiment of FIG. 5.
Figure 7:
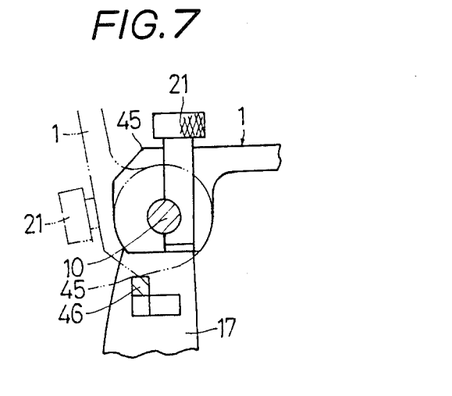
FIG. 7 is a sectional view of the clamping portion of the condyle path plate.

FIG. 6 shows another example of the rear wall 6 described with reference to FIG. 5. The rear wall 6 is provided at the front adjustment screw 12, and is telescoped longitudinally with respect to the front adjustment screw sleeve 44 by operating the knob 43. Reference numeral 22 illustrates a rear wall support similar to the above support and the other construction is the same as before.

The upper jaw arciform 1 has an engaging projection 45 at the rear center to be engaged with an upper jaw arciform inverting time opening stopper 46 mounted between the posts 17 and 18, thereby preventing the projection 45 from being disengaged from the stopper 46 due to incomplete inversion. Further, reference numerals 47 and 48 designate mounting plates for models of upper and lower jaws, numeral 49 depicts a clamping screw of the upper jaw model, numeral 50 indicates a gypsum drop preventing plate of the lower jaw model mounting portion, numeral 51 illustrates pins for selectively fastening the positions of the lower jaw model mounting plate 48 at the front and rear positions, numeral 52 designates engaging holes of the pin 51 and an engaging pin 53, numeral 54 depicts a screw engaged with the mounting plate 48, numeral 55 indicates female threads to be engaged with the screw 54, and numeral 56 illustrates a spring interposed between the threaded head 54a and the lower jaw arciform 2. Numeral 57 designates an upper jaw opening holder mounted via a clamping screw 58 to the front end of the upper jaw arciform 1, numeral 59 depicts an incisal pin adjustably mounted by an upper jaw opening angle clamping screw 60, numeral 61 indicates an incisal pin tip, numerals 62, 62 illustrate a pair of incisal tables mounted by a table fastening screw 63 to the front end of the lower jaw arciform 2. The table 62 is disposed laterally in a table frame 65 rockably supported to a table base 64, supported at the front and rear sides of the center by a support 66 to be movable at both ends, suitably clamped by a knob 69 to be engaged with threaded rods 68 respectively projected from the side holes 67, 67 of the frame 65. The frame 65 is forwardly tiltably supported by a shaft 70 to the table base 64, and clamped at a predetermined position by a screw 72 engaged with the frame 65 via an arcuate hole 71. Numeral 73 designates a centric lock plate, numeral 74 depicts its clamping screw, and numeral 75 indicate scales of movable units.

The operation of the articulator of the invention constructed as described above will be described. When the upper jaw arciform 1 is mounted on the lower jaw arciform 2 by placing the condyle path plate 5 on the condylar sphere 4 from the rear and the scales of the portions are set to zero points, the incisal pin tip 61 is the disposed at the center of the incisal table 62. The upper and lower jaw models are then respectively mounted on the mounting plates 47 and 48, the biting state of the person is reproduced in the articulator by a check biting method, thereby adjusting the condyle path to the intrinsic value.

Since the biting state of a person is already determined to manufacture a partial denture such as, for example, a crown bridge, necessary measurements are carried out with the biting surface as a reference. In this case, it is necessary to readily separate upper and lower arciforms. Thus, the lower wall 9 of the articulator of this invention is removed and the articulator is used as an archon box type. When the lower wall 9 is removed, the condyle path can be simply adjusted without fabricating a split cast. In order to manufacture a dental prosthesis, the lower wall 9 is attached to prevent the condylar sphere 4 from floating from the condyle path plate 5 to be used as a slot type. Thus, the arrangement and the grinding of the denture can be reliably effected and facilitated.

FIGS. 11 to 17 show another embodiment of an articulator according to this invention. Reference numeral 101 designates an upper jaw unit, numeral 102 depicts a lower jaw unit, the upper unit 101 has an upper jaw model arciform 114, and the lower unit 102 has a lower jaw model arciform 115. The arciform 114 is mounted through condylar spheres 105, 106 at the base ends at condyle shafts 107, 108 engaged adjustably at an interval on two posts 103 and 104 stood from the lower jaw unit 102. The shafts 107, 108 respectively have condylar spheres 105 and 106 at the ends, are engaged telescopically into sleeves 116, 117 engaged with the posts 103, 104 at the threaded portions 107a, 108a. Numerals 118 and 119 designate knobs, and 118a, 119a depict scales. The spheres 105 and 106 are respectively rotatably mounted in grooves c formed on the shafts 107 and 108 via screws b. Inverted L shaped condyle path frames 120 and 121 are mounted rockably in upward and downward directions at both ends of the base of the upper jaw unit 101 at both ends of the base of the upper unit 101, and the condyle path member 112 is rockably supported with the sidewisely movable shaft 113 as a shaft. The upper unit 101 is rockably at approx. 80° upward of an arrow and approx −5° downward, and the supporting shafts of the frames 120, 121 are clamped by clamping screws 120a, 121a within the abovementioned range.

In the embodiment of the articulator of the invention shown in FIGS. 11 to 15, the condyle path member 112 is associated in U shape as observed from the front at the upper wall 109, and the lower wall 110 and the inside wall 11, and mounted rockably to a vertical hole 122 of the frames 120, 121 through sidewisely movable shaft 113 projected to the member of the upper wall 109. Numeral 113a designates a side condyle path inclining angle indicator fastened to the shaft 113, numeral 113b depicts a washer, numerals 122a indicates a side condyle path inclining angle adjusting knob, and numeral 122b illustrates the same inclining angle scale. Numeral 123 illustrates a condyle path rear frame suspended to the rear side of the frames 120, 121, numeral 124 designates a condyle path rear wall mounted longitudinally movably through the front adjustable shaft 124a to the rear frame 123, which is contacted with the spheres 105, 106. Numeral 126 depicts a front adjusting knob engaged with the adjustable shaft 124a, numeral 125a indicates a scale, numeral 126 illustrates a front adjustable screw sleeve, numeral 127 designates an upper jaw model frame, numeral 128 indicates a table, numeral 129 depicts a hanging rod, and numeral 130 illustrates a guide board.

Figure 16:
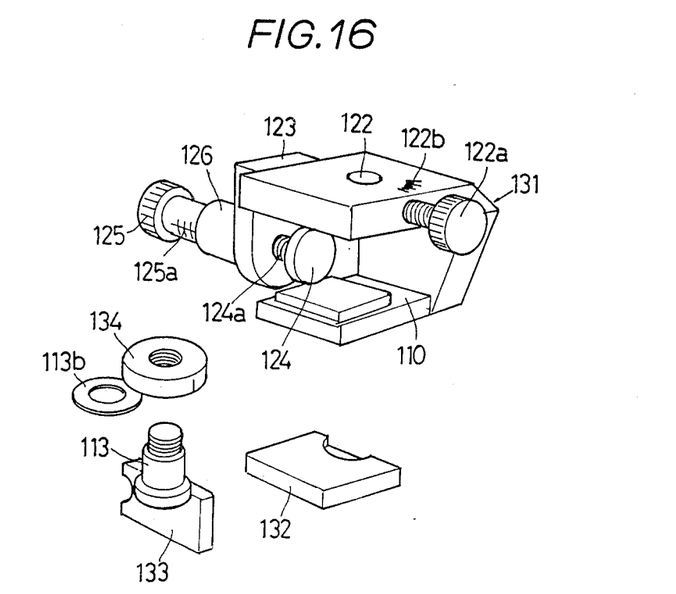
FIG. 16 is an exploded perspective view of a modified embodiment of this invention.
Figure 17:
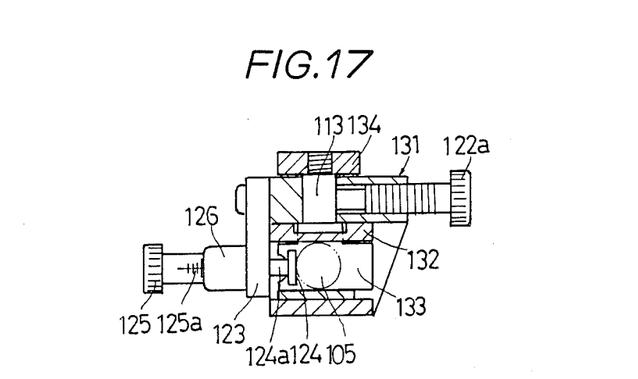
FIG. 17 is a sectional view of the condyle path.

FIGS. 16 and 17 show another example of a condyle path member 112. A condyle path frame 131 is formed substantially in U shaped cross section having a lower wall 110. The upper wall may be formed with the frame 131 as the upper wall, but, since the upper wall is ordinarily formed of aluminum, an upper wall member 132 of another material such as brass is used to reinforce the strength, and a side condyle path inclining angle restricting plate 133 mounted in the same manner as described above becomes the inner wall 111 by the side movable shaft 113 to the frame 131. Numeral 134 designates a side condyle path inclining angle regulating knob, and the other construction may be the same as before, and the same symbols are attached to the corresponding components, and the description will be omitted. The side inclining angle is adjustable in a range of approx. 0° to 30°.

In the construction of the articulator according to the invention described above, the left and right condylar spheres 105 and 106 are held at the upper jaw unit 101 with the lower jaw unit 102 in the state contacted with the upper wall 109 and the lower wall 110 of the condyle path member 112. The condylar spheres 105, 106 can be contacted with the upper wall 109, the lower wall 110, the inside wall 11 and the rear wall 124. When the forward adjustable shaft 124a is held and adjusted by the operation of the knob 125, the rear wall 124 is longitudinally moved backward and forward, the condylar spheres 105 and 106 are contacted with the inside wall 111 at the point that the center of the spheres 105 and 106 coincide with the center of the side movable shaft 113. Even if the side condyle path inclining angle is altered by the operation of the knob 122a, the spheres can be always contacted with the inside wall 111, and this point is accordingly set to zero point. On the other hand, the length between the condyles of the lower jaw model arciform 115 can be separately altered at the right and left sides in the lengths from the lower jaw arciform to the condyles 105 and 106 by operating the knobs 118, 119. Accordingly, the left and right condylar spheres 105, 106 can be separately isolated from the left and right inside walls 111 irrespective of the adjustment of the side inclining angle of the condyle path member 112 eve if the forward adjustable shaft 142a is set to the zero point. Since the forward adjustable shaft 124a is held in the rear frame 123 at this time, the front and rear positions of the upper jaw unit 101 and the lower jaw model arciform 115 can be held.

What is claimed is:

1. An articulator convertible between an archon box type and an archon slot type, comprising:
    an upper jaw arciform and a lower jaw arciform for mounting a gypsum model;
    a pair of right and left condylar spheres provided at the rear of the lower jaw arciform;
    condyle path plates provided at the rear of the upper jaw arciform for supporting the condylar spheres;
    the condyle path plates including a rear wall contacting the rears of the condyle spheres, side walls contacting the sides of the condyle spheres and a lower wall contacting the lower portion for preventing the condyle path plate from floating; said lower wall being detachable;
    whereby attachment and removal of said lower wall permits conversion, respectively, between an archon slot type and an archon box type.

2. An articulator according to claim 1, wherein said condyle path plates can rotate as a whole around a shaft coincident to the center of the condylar sphere, and pivotally secured to the upper jaw arciform via a shaft to alter the condyle path inclining angle of arrow shape.

3. An articulator according to claim 1, wherein the lower wall is mounted detachably by a clamping screw to a rotary member or the upper jaw arciform.

4. An articulator having dentures mounted on upper ad lower jaw units for deciding the biting state of the dentures, comprising:
    posts disposed at the right and left sides of a base of the lower jaw unit, a condyle shaft having condylar spheres at the ends thereof and which is mounted oppositely to the upper ends of said posts, condyle path frames mounted rockably at both ends of the base of said upper jaw unit, condyle path members formed of upper wall and inside wall with the spheres filled in the frames, said condyle path members being supported through a sidewardly movable shaft to hold the spheres rockably in contact with the upper, lower and inside walls; and a rear wall provided at the rear of the condyle path members for telescopically moving the spheres.

* * * * *